US009220399B2

(12) United States Patent
Cinquin et al.

(10) Patent No.: US 9,220,399 B2
(45) Date of Patent: Dec. 29, 2015

(54) IMAGING SYSTEM FOR THREE-DIMENSIONAL OBSERVATION OF AN OPERATIVE SITE

(75) Inventors: Philippe Cinquin, St. Nazaire les Eymes (FR); Sandrine Voros, Sevres (FR); Christophe Boschet, Le Garde (FR); Céline Fouard, Grenoble (FR); Alexandre Moreau-Gaudry, Grenoble (FR)

(73) Assignee: CONSTELLIUM FRANCE, Paris (FR)

( * ) Notice: Subject to any disclaimer, the term of this patent is extended or adjusted under 35 U.S.C. 154(b) by 880 days.

(21) Appl. No.: 12/674,594

(22) PCT Filed: Aug. 20, 2008

(86) PCT No.: PCT/EP2008/060871
§ 371 (c)(1),
(2), (4) Date: Feb. 22, 2010

(87) PCT Pub. No.: WO2009/027278
PCT Pub. Date: Mar. 5, 2009

(65) Prior Publication Data
US 2011/0122229 A1 May 26, 2011

(30) Foreign Application Priority Data
Aug. 24, 2007 (FR) ..................... 07 57160

(51) Int. Cl.
*H04N 13/00* (2006.01)
*A61B 1/04* (2006.01)
*A61B 1/00* (2006.01)

(52) U.S. Cl.
CPC ............. *A61B 1/042* (2013.01); *A61B 1/00193* (2013.01)

(58) Field of Classification Search
CPC ..... H04N 7/18; H04N 13/02; H04N 13/0239; H04N 2005/2255; H04N 13/0296; H04N 13/0055; A61B 1/00193
USPC ............ 348/45, 77; 359/377, 466; 128/653.1; 600/111, 166, 476, 102, 316.2; 73/644; 606/130

IPC ....................................................... H04N 13/00
See application file for complete search history.

(56) References Cited

U.S. PATENT DOCUMENTS 4,977,780 A * 12/1990 Machida et al. ................ 73/644
5,191,130 A   3/1993 Sanderson et al.
(Continued)

FOREIGN PATENT DOCUMENTS

| EP | 1 690 497 A1 | 8/2006 |
| EP | 1690497 | 8/2006 |

(Continued)

OTHER PUBLICATIONS

Franco et al.; "A Voice Controlled Robotic Arm for Endoscopic Surgery"; Recommendations Du Cedit; Cedit APHP.FR; 2002.
(Continued)

*Primary Examiner* — Thao X Le
*Assistant Examiner* — Long Le
(74) *Attorney, Agent, or Firm* — Miles and Stockbridge

(57) ABSTRACT

The invention relates to an endoscopic imaging system for observation of an operative site (2) inside a volume (1) located inside the body of an animal, comprising:
   Image capture means (3) intended to provide data on the operative site (2),
   Processing means (4) to process data derived from the image capture means,
   Display means (5) displaying data processed by the processing means (4), characterized in that: The image capture means (3) comprise at least two image capture devices that are independent and mobile relative to one another, the image capture devices being intended to be positioned inside the volume (1), and in that:
   The processing means (4) comprise computing means to obtain three-dimensional data on the observed operative site (2) from data provided by the image capture devices, and means to reconstruct a three-dimensional image of a region of interest of the operative site from the three-dimensional data obtained.

14 Claims, 3 Drawing Sheets

(56) References Cited

U.S. PATENT DOCUMENTS

| | | | | |
|---|---|---|---|---|
| 5,647,838 | A | * | 7/1997 | Bloomer ................. 600/111 |
| 5,749,362 | A | * | 5/1998 | Funda et al. ............ 600/407 |
| 5,792,147 | A | | 8/1998 | Evans et al. |
| 6,146,390 | A | | 11/2000 | Heilbrun et al. |
| 6,591,130 | B2 | | 7/2003 | Shahidi |
| 2004/0002627 | A1 | | 1/2004 | Igarashi |
| 2005/0096502 | A1 | * | 5/2005 | Khalili ..................... 600/106 |
| 2005/0234294 | A1 | | 10/2005 | Saadat et al. |
| 2008/0147018 | A1 | * | 6/2008 | Squilla et al. ............ 604/264 |
| 2009/0259102 | A1 | * | 10/2009 | Koninckx et al. ........ 600/111 |
| 2010/0256504 | A1 | * | 10/2010 | Moreau-Gaudry et al. .. 600/476 |
| 2011/0202070 | A1 | * | 8/2011 | Dario et al. .............. 606/130 |

FOREIGN PATENT DOCUMENTS

| | | |
|---|---|---|
| WO | 2007/078003 | 7/2007 |
| WO | 2007/078003 A1 | 12/2007 |

OTHER PUBLICATIONS

Menier et al.; "A Distributed Approach for Real Time 3D Modeling"; Inria Rhones-Alpes; May 2005.

Dombre et al.; "Gabie Project: Ultra Sound Based Active Guidance"; Actes Des Journees Robea, Montpellier; Mar. 2005; pp. 49-56 (Abstract Only).

Garcia et al.; "Equipment and 3D-Vision,"; Operative Techniques on Websurg; Sep. 2004.

Devernay et al.; "Structured Light on Dynamic Scenes Using Standard Stereoscopy Algorithms"; Feb. 1997; 16 Pages (With English Abstract).

Dornika; "Contributions to the Integration of Vision and Robotics: Calibration, Localization, and Servoing"; Inria Rhones-Alpes; Sep. 25, 1995 (Abstract).

Nicolau; "An Augmented Reality System to Guide Liver Percutaneous Punctures"; Instititut National De Recherche En Informatique Et Automatique; Nov. 4, 2004 (Abstract).

Rentschler et al.; "Mobile In Vivo Camera Robots Provide Sole Visual Feedback for Abdominal Exploration and Cholecystectomy"; Surg. Endosc.; 20: 135-138; 2006.

Sobel et al.; "A 3×3 Isotropic Gradient Operator for Image Processing"; [Presented at a Talk at the Stanford Artificial Project in 1968, Unpublished But Cited, Orig. in Pattern Classification and Scene Analysis, Duda, R. and Hart, P.; John Wiley and Sons, '73]; pp. 271-272; Published in 1973.

Bradski et al.; "Intel's Computer Vision Library: Applications in Calibration, Stereo, Segmentation, Tracking, Gesture, Face and Object Recognition"; Library of Image Processing (http://www.intel.com/technology/computing/opencv/); 2000.

Library of Image Processing "Camera Calibration Toolbox for Matlab" (http://www.vision.caltech.edu/bouguetj/calib_doc/) Chapters 1-13; [Presented in 2000 in a Technical Report at the California Institute of Technology (CALTECH)]; 2000.

B. Makhoul, et al., "Laparoscopic Radical Nephrectomy for T1 Renal Cancer: The Gold Standard? A Comparison of Laparoscopic vs Open Nephrectomy"; BJU International, vol. 93, pp. 67-70, 2004.

M. E. Moran, "Robotic Surgery: Urologic Implications"; Journal Endourology, Nov. 2003; vol. 17, No. 9.

P. Ballester, et al.; "Comparison of Task Performance of Robotic Camera Holders"; International Congress Series; 2001, vol. 1230, pp. 1100-1103.

L. R. Kavoussi, et al., "Comparison of Robotic Versus Human Laparoscopic Camera Control", The Journal of Urology, Dec. 1995, vol. 154, pp. 2134-2136.

S. Aiono, et al., "Controlled Trial of the Introduction of a Robotic Camera Assistant (Endoassist) for Laparoscopic Cholecystectomy", Surg Endosc.; 2002; vol. 16; pp. 1267-1270.

E. J. Hanly, et al.; "Robotic Abdominal Surgery", The American Journal of Surgery 188 (Suppl to Oct. 2004) 19S-26S.

M. Hashizume, et al.; "Robotic Surgery and Cancer: The Present State, Problems and Future Vision"; Japanese Journal of Clinical Oncology, 2004, vol. 34, No. 5, pp. 227-237.

P. Berkelman, et al.; "Development and Testing of a Compact Endoscope Manipulator for Minimally Invasive Surgery"; Computer Aided Surgery, 2005, vol. 10, No. 1; pp. 1-13.

D.Oleynikov, et al.; "Miniature Robots Can Assist in Laparoscopic Cholecystectomy", Surgical Endoscopy, 2005, vol. 19; pp. 473-476.

M. Rentschler, et al.; "Modeling, Analysis, and Experimental Study of In Vivo Wheeled Robotic Mobility", Robotics IEEE Transactions, Apr. 2006, vol. 22, No. 2, pp. 308-321.

F.Devernay, et al.; "Structured Light on Dynamic Scenes Using Standard Stereoscopy Algorithms"; Thème 4 : Simulation Et Optimisation De Systèmes Complexes. Projet Chir. Rapport De Recherche Inria Sophia Antipolis, N°4477, Jun. 2002, 19 Pages.

M. Chan, et al.; "Miniaturized Three-Dimensional Endoscopic Imaging System Based on Active Stereovision", Applied Optics; Apr. 2003; vol. 42, No. 10; pp. 1888-1898.

N. A. Dodgson, et al.; "Autostereoscopic 3D Display in Laparoscopic Surgery", CAR '95 (Computer Assisted Radiology), Jun. 21-24, 1995; pp. 1139-1144, Berlin.

Z. Zhang, et al.; "A Flexible New Technique for Camera Calibration"; IEEE Transactions on Pattern Analysis and Machine Intelligence, 2000, vol. 22; No. 11; pp. 1330-1334.

W. Avenhaus, et al.; "Dynamic Holographic Endoscopy—Ex Vivo Investigations of Malignant Tumors in the Human Stomach"; Lasers in Medical Science, Apr. 2005, vol. 19, No. 4, pp. 223-228.

S.Voros, et al.; "Automatic Localization of Laparoscopic Instruments for the Visual Servoing of an Endoscopic Camera Holder"; 9th Miccai Conference Copenhagen, Oct. 1-6, 2006; pp. 535-542.

A. A. Montenegro, et al.; "Adaptative Space Carving, 2nd International Symposium on 3D Data Processing"; Visualization and Transmission (3DPVT), Sep. 6-9, 2004; 8 Pages.

O. Faugeras Ntitulée << Three-Dimensional Computer Vision—A Geometric Viewpoint >> (The MIT Press, Cambridge, MA, USA, 1993) pp. 33-243 (Chapters 3 and 6).

J. Canny; "A Computational Approach to Edge Detection"; IEEE Transactions on Pattern Analysis and Machine Intelligence, vol. PAMI-8; Nov. 1986; No. 6, pp. 679-698.

C. Harris et al.; "A Combined Corner and Edge Detector"; 1988, pp. 147-151; Plessey Research Roke Manor, UK.

R.I. Hartley et al.; "Trianglulation"; Computer Vision and Image Understanding, Nov. 1997, vol. 68; No. 2, Article IV970547; pp. 146-157.

E. Prados, et al.; "Shape From Shading"; Handbook of Mathematical Models in Computer Vision Springer; 2006; pp. 375-388.

R. Horaud, et al.; "Hand-Eye Calibration"; The International Journal of Robotics Research; Jun. 1995; vol. 14, No. 3, pp. 195-210.

R.I. Hartley, A. Zisserman << Multiple View Geometry in Computer Vision >> (Cambridge University Press, 2000) pp. 152-324 (Chapters 6-7 and 9-12).

International Search Report, PCT/EP2008/060871, Nov. 28, 2008 (6 pages).

Horaud et al., "Hand-Eye Calibration," Int. Journal of Robotics Research, Jun. 1995, vol. 14, No. 3, pp. 195-210.

Zhang et al., "A Flexible New Technique for Camera Calibration," IEEE Transactions on Pattern Analysis and Machine Intelligence, Nov. 2000, vol. 22, No. 11, pp. 1330-1334.

* cited by examiner

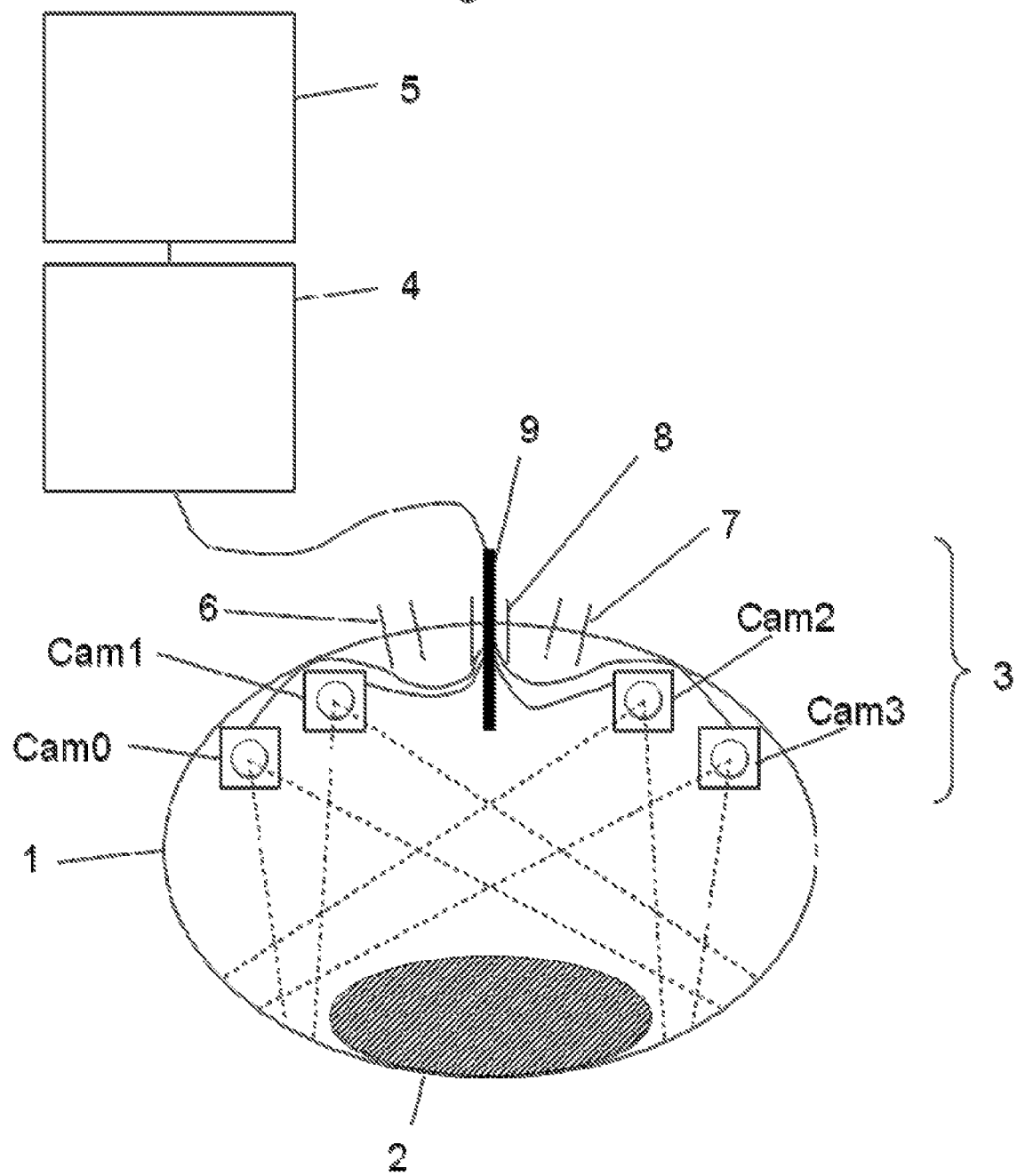

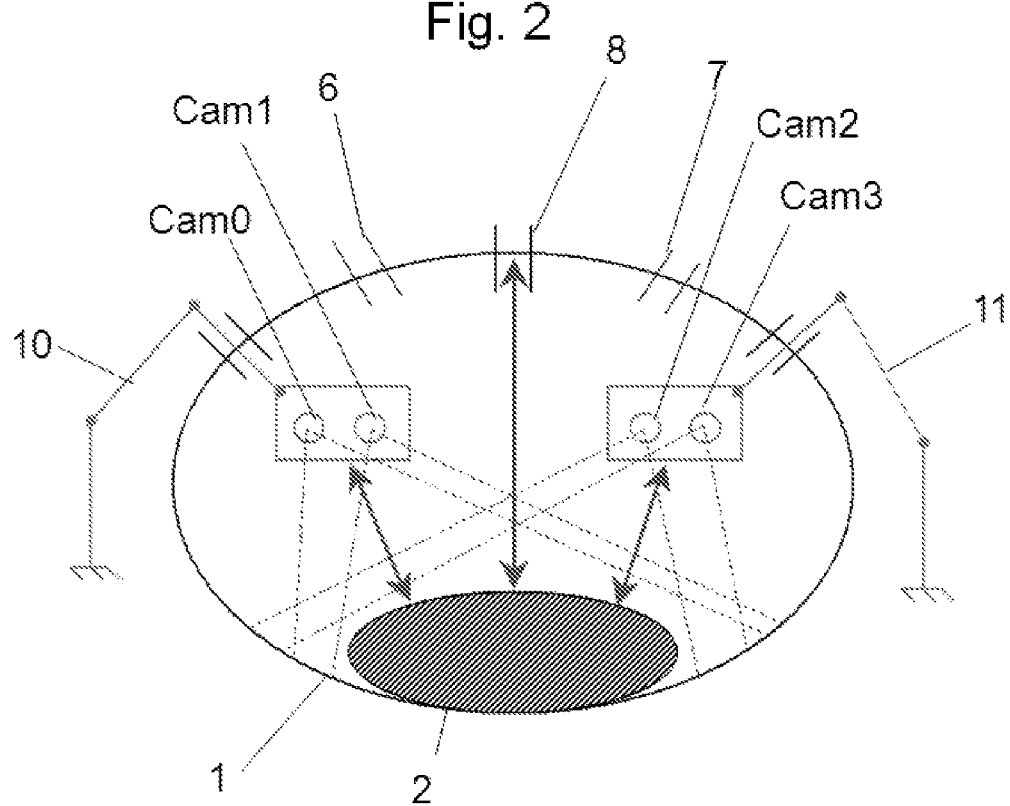
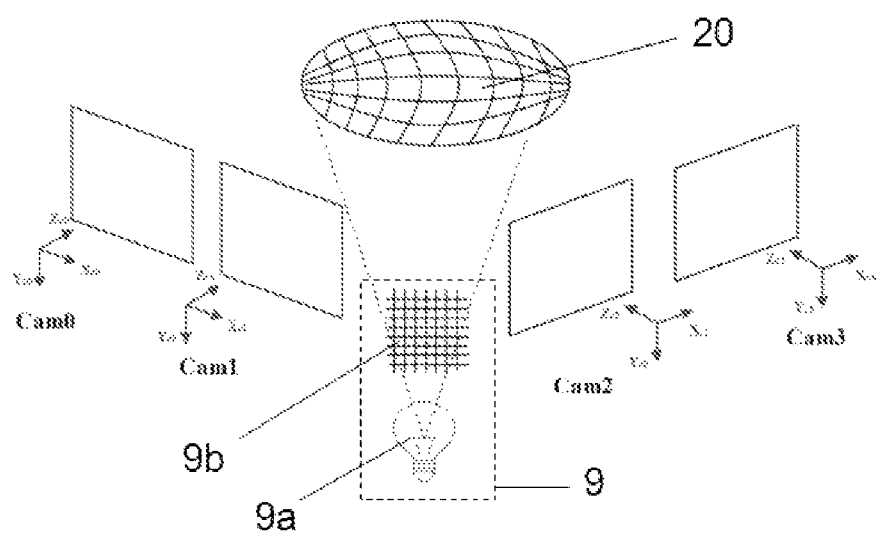

IMAGING SYSTEM FOR THREE-DIMENSIONAL OBSERVATION OF AN OPERATIVE SITE

CROSS REFERENCE TO RELATED APPLICATIONS

This application is a National Phase of PCT/EP2008/060871 filed Aug. 20, 2008, which claims priority to FR 0757160 filed Aug. 24, 2007.

BACKGROUND OF THE INVENTION

1. Field of the Invention

The present invention relates to the field of medical imaging and more particularly the viewing of body organs under endoscopy during surgical operations.

2. State of the Art

Surgical endoscopy is a minimally invasive medical investigation technique which, whilst ensuring repair that is identical to conventional techniques, can reduce the size of incisions and limit regions of dissection. It is called laparoscopy for minimally invasive surgery via the abdominal cavity. This surgical technique considerably reduces operative trauma, risks of complications, pain and patient recovery time, and limits cosmetic impairment.

Endoscopy nonetheless remains difficult to carry out and requires specific learning procedures. For the surgeon, a direct view of the operative site is replaced by a 2D image on a monitoring screen via an endoscope, with the limitations this entails: imperfect illumination, shadowy regions, difficult perception of reliefs, limited field of vision, possible occlusions with instruments hidden by organs. This viewing system may contain geometric deformations and has limited resolution, contrast and colour.

Different three-dimensional (3D) viewing systems have therefore been developed to re-create perception of depth so as to improve visualization of body organs at the operative site.

The simplest and most economical solution to cause depth to appear in an endoscopic image is to create shadows. By adding indirect light in addition to the light source located at the end of the endoscope, it is possible to project shadows onto the viewed structures, thereby recreating a new sense of depth. Said viewing system gives poor performance however and does not provide satisfactory image quality for the practitioner.

Another solution consists of using a stereo-endoscope coupled with polarizing glasses. A stereo-endoscope consists of a single endoscope in which two separate optical systems are assembled and two cameras, allowing slightly different images to be captured of one same region, and thereby imitating human vision. The images given by the stereo-endoscope are then alternately projected onto a single screen at a frequency of 100 Hz. The screen is polarized vertically and then horizontally by an active polarizing filter. The polarizing glasses have one glass polarized vertically and another polarized horizontally so that each eye only receives one of these two images, thereby providing the surgeon with a 3D view of the region under observation. Nonetheless, this type of system comprises a certain number of disadvantages, related firstly to the stereo-endoscope, which only permits observations over very short distances, and secondly to the use of glasses which cause eye fatigue, which means that this solution can scarcely be used for operations which may last several hours. In addition, the image quality remains inferior to existing two-dimensional (2D) viewing systems.

A 3D endoscopic imaging system using structured light has also been developed. It consists of two channels, one allowing an image to be obtained, the other allowing projection of structured light. Light structuring consists of projecting light, generally a white light, through line arrays so as to create a frame on the object to be acquired. The object is viewed by a camera such as a CCD camera (charge coupled device) which observes the object through a slightly offset frame so as to create a Moiré effect. The distribution and intensity of this effect enhance the volume of the object and allow acquisition of the third dimension. However, said system is difficult to implement and above all it is costly.

In addition to the drawbacks already cited for each of the existing 3D viewing systems, these systems do not offer expected quality of viewing, some visual discomfort always being present. Since endoscopic surgery already entails major constraints, 2D viewing systems are more reliable, and therefore remain the preferred choice of surgeons despite the drawbacks related to their use.

Finally, most viewing tools for endoscopic surgery are relatively complex to use since, in addition to carrying out surgical movements, the practitioner must also move the endoscope in relation to the desired field of vision or give orders to an assistant to move the endoscope into the desired field of vision.

One purpose of the present invention is therefore to propose an endoscopic imaging system permitting three-dimensional viewing of an operative site, which is simple and is able to solve at least one of the above-cited disadvantages.

DISCLOSURE OF THE INVENTION

For this purpose, an endoscopic imaging system is proposed to observe an operative site within a volume located inside the body of an animal, comprising:

Image capture means intended to provide data on the operative site,

Processing means to process the data derived from the image capture means,

Display means to display the data processed by the processing means, characterized in that:

The image capture means comprise at least two image capture devices that are independent of each other and mobile with respect to each other, the image capture devices being intended to be positioned within the volume, and in that The processing means comprise computing means to obtain three-dimensional data on the observed operative site from the data received from the image capture devices, and reconstruction means to reconstruct a three-dimensional image of a region of interest in the operative site from the three-dimensional data obtained.

Preferred, but non-limiting aspects of the endoscopic system are the following:

the image capture devices are ultrasound probes;
the image capture devices are cameras;
the cameras are in movement each relative to the other;
the processing means further comprise synthesis means to synthesize an image of the region of interest, said synthesizing means comprising means to merge the reconstructed three-dimensional image of the region of interest with data provided by the camera on the region of interest, said data being interpolated at the desired resolution level;
the region of interest corresponds to the operative site as a whole;

the system further comprises means to select a viewing angle, the display means comprising means to display the three-dimensional image corresponding to the selected viewing angle;

the system further comprises means to determine the relative position of the cameras;

the means to determine the relative position comprise a magnetic positioning device to locate the cameras;

the means to determine the relative position comprise an optical locating device to locate the cameras, based on data given by the cameras;

the optic locating device to locate the cameras comprises a reference element arranged so that it is able to be seen by at least two cameras;

the optic locating device to locate the cameras comprises at least two reference cameras arranged so that they can see the other cameras;

the reference cameras are located outside the volume, each of the cameras located inside the volume being coupled with a non-deformable member, the non-deformable member having one part extending outside the volume so that it can be seen by the reference cameras;

the means to determine the relative position comprise means to project a texture onto the operative site so as to form a reference system for the cameras;

the cameras are cameras having a volume of less than 5 $mm^3$;

each camera comprises an attachment device adapted to hold the camera in place in the volume;

the attachment device comprises a first element fixed to the camera and a second separate element, the first and second elements able to be magnetically coupled, the second element being intended to remain outside the volume;

the system further comprises a mechanical structure intended to be placed inside the volume to hold the cameras in position;

the mechanical structure is a structure adapted so that it can be inserted via endoscopic route into the volume and is able to be deployed inside the volume;

the image capturing means comprise at least three cameras, two of these three cameras being attached to an instrument intended to be inserted inside the volume.

BRIEF DESCRIPTION OF THE FIGURES

Other characteristics and advantages will become further apparent from the following description which is solely illustrative and non-limiting, and is to be read with reference to the appended figures amongst which:

FIG. 1 is a schematic illustration of an endoscopic imaging system according to one embodiment of the invention;

FIG. 2 is a schematic illustration of the endoscopic imaging system according to another embodiment of the invention;

FIG. 4 is a schematic illustration of the endoscopic imaging system according to the invention with a projection device to determine the relative position of the cameras.

DETAILED DESCRIPTION OF THE INVENTION

Figure 3:
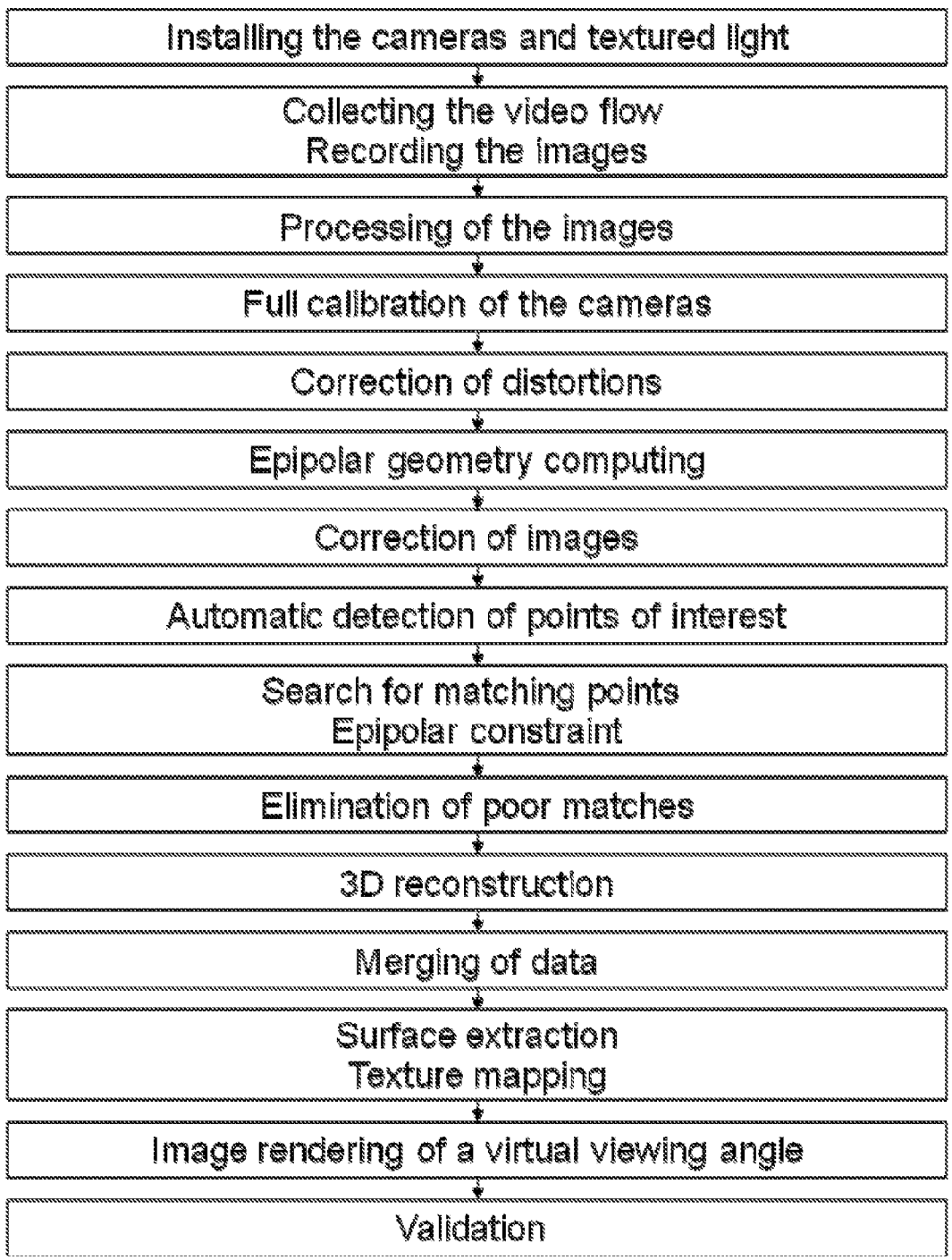
FIG. 3 is a diagram illustrating the functioning of the endoscopic imaging system.

FIG. 1 is a schematic illustration of the proposed endoscopic imaging system.

This imaging system comprises image capture means 3 which are adapted so that they can be inserted via endoscopic route into a volume 1 located inside the body of an animal such as a human being, requiring surgery, as far as the operative site 2. This volume 1 or volumetric region forms a cavity 1, this cavity being natural or artificial in which case it is created by injecting air into the volume.

The image capture means 3 are linked to data processing means 4 which are typically a central unit provided with computing means such as a microprocessor, so that they are able to process information provided by the image capture means 3.

The processing means 4 are also coupled with display means 5 which allow visualization of the data provided by the processing means 4, this data typically being three-dimensional data of the operative site 2 so that the practitioner is able to view the operative site 2 at the same time as performing surgery.

As schematically illustrated in FIG. 1, one or more incisions are made in the cavity 1, which are used to insert the surgical instruments and through which the image capture means are also inserted. These incisions are made using trocars (6; 7; 8) which are inserted through the wall forming the cavity 1.

Typically two trocars (6; 7) are provided dedicated to passing the practitioner's instruments (not shown) during surgery.

In addition, at least one additional trocar 8 is provided for the insertion of the image capture means 3 into the cavity 1, so that it is possible to view the region of interest in the operative site 2. It is to be noted however that it could be considered to insert the image capture means through the two trocars (6; 7) intended for the instruments without necessitating a dedicated trocar 8.

The image capture means 3 of the proposed endoscopic imaging system comprise a plurality of image capture devices intended to be inserted and deployed inside the cavity 1 of the patient. Preferably, as image devices, use is made of cameras. Even if the remainder of the description refers to this embodiment, other devices may be used such as ultrasound imaging devices of ultrasonic probe type.

The principle is therefore to arrange a certain number of cameras inside the cavity 1 so that it is possible to obtain three-dimensional data on the operative site 2 from several viewpoints, without having to move the cameras as is the case for all known non-invasive solutions.

One particular embodiment of the invention consists of coupling these cameras two by two thereby forming a plurality of pairs of cameras. Each pair of cameras forms a stereoscopic viewing system, the data collected by these cameras able to be correlated to provide 3D information on a particular region of the operative site 2. Stereoscopic viewing forms a priority approach for the rendering of 3D perception. It is based on binocular deviation: each eye captures a vision of the world from a different viewing angle. By causing the deviations of the two images to correspond, it is possible to estimate the distance between the observed objects and the observation point. For computer viewing, two images are used taken by two cameras instead of images perceived by each of the two eyes. Adequate processing of these images allows 3D information to be obtained on a particular observed region, even a whole reconstruction of the 3D image of the observed region. This computer reconstruction is particularly advantageous since it allows a 3D representation of the operative site to be given directly to the surgeon, without any mental effort being required of the surgeon to carry out this representation. It also provides a basis from which it is possible to choose any virtual viewpoint and the best adapted illumination conditions using conventional "image synthesis" techniques. More details will be given below on the functioning of the stereoscopic sensor formed by each pair of cameras.

The image capture means 3 therefore comprise several small-sized cameras which can be inserted in the cavity 1 via a trocar passed through the wall of the cavity 1. The volume of the cameras is typically a few cubic millimeters ($mm^3$), preferably less than 5 $mm^3$. Also, the cameras used have high-performance optics based on CMOS technologies (Complementary Metal-Oxide Semiconductor) or CCD technologies (Charge-Coupled Device).

The cameras are independent of each other i.e. they are separate and operate independently. They are also mobile relative to one another which means that they can be caused to move within the cavity 1 without compromising the functioning of the endoscopic imaging system.

The example in FIG. 1 illustrates an imaging system comprising 4 cameras (Cam0, Cam1, Cam2, Cam3). Each of these cameras is inserted via the trocar 8, then attached inside the cavity 1 by any attachment means either directly onto the inner wall of the cavity 1, or onto an organ close to the operative site 2. Amongst attachment means, suction systems are of particular interest to attach cameras to some organs or onto the inner wall of the cavity 1. Each camera may also be provided with a magnet which holds it flat against the inner wall of the cavity 1, provided another magnet is positioned opposite the camera on the outer wall of the cavity. In addition to the attaching function, this will also allow easy movement of the camera should this become necessary for a particular surgical task.

The cameras are arranged so as to provide an accumulated field of vision covering the entire operative site, 2 from several viewing angles. The arrangement of these cameras evidently depends on the size of the operative site 2, but also on the technical characteristics of the cameras such as field of vision, depth of field and the type of lens used.

Preferably, at least three cameras are used so that it is possible to access hidden regions of the operative site (non-visible with a mono or stereo-endoscope) and to increase the number of data on this operative site. This provides widening of the surgeon's virtual field of vision by providing additional data without having to move the cameras. The proposed system is additionally not subject to the arrangement constraints characterizing stereo endoscopic systems, for which it is necessary for example for the two cameras used to lie very close to each other. Therefore, it is possible to have cameras that are relatively distant from one another, this not being a hindrance for reconstruction of 3D representation of the operative site.

It is also possible to attach one or even two cameras to one of the instruments (or to each instrument) that is to be inserted inside the cavity 1 via one of the trocars (5; 6) provided for this purpose. These cameras positioned on the instrument complement the camera or cameras positioned inside the cavity 1.

In the embodiment illustrated in FIG. 1, the cameras are inserted via a trocar 8 which is then used to insert projection means 9 to project a textured image onto the operative site. These projection means 9 enhance the natural texture of the organs observed by the cameras. In some cases, these organs are effectively relatively homogeneous giving rise to difficult identification of the points of interest (this is particularly the case for the surface of the liver). Yet, said points are important for our approach. As will be seen further on, we need to substantiate points on the organs which can be seen by several cameras at the same time to permit determination of the relative position of the cameras, and also to permit matching the projection of these points in at least two cameras, which will make it possible to reconstruct the 3D coordinates of these said points.

As illustrated in FIG. 4, the projection means 9 comprise a light source 9a (for example a conventional cold light source in endoscopy, or a light-emitting diode). This source 9a illuminates the scene through an inhomogeneous object 9b which therefore creates a texture 20. This object 9b may for example be a lens on which patterns are etched. The characteristics of the lens and patterns are calculated so that when the organs are illuminated by the projection system 9 a pattern as precise as possible can be obtained e.g. a grid. However, it is not necessary for this pattern to be perfectly focused, all that is required is information allowing matching of the points in the various cameras observing the scene.

It is noted that it is possible to insert the cameras and the projection means 9 via the orifices used to insert the surgical instruments, thereby eliminating the need for one of the skin openings if it is not needed for another purpose such as determination of the relative position of the cameras. Therefore, an orifice specifically dedicated to the image capture means 3 is not necessarily needed as is the case with known endoscopic imaging systems.

To reinforce the natural texture of the observed body organs, a laser fibre source of green colour can also be used that is provided with a special diffractive optic. This optic shapes the light and allows the projection of an array of lines or dots onto the surface of the organs of the operative site, so that the light enhances the natural texture of the organs whilst disclosing their shapes. The green colour of the laser is particularly suitable for endoscopic surgery. The images derived from the abdominal cavity for example effectively have a tendency to show a dominant colour in red or pink shades, the green light therefore provides a particular contrast. Additionally, the laser fibre solution allows the laser source to be kept outside the cavity of the operative site. The end of the optic fibre consists of a small reinforcement comprising the special diffractive optic. It is this reinforced part that is inserted in the abdominal cavity via a trocar.

Attachment of the cameras in the cavity 1 may also be obtained using a dedicated mechanical structure. Said embodiment is illustrated by the example in FIG. 2. In this embodiment, additional incisions are provided used to position trocars via which mechanical structures (10; 11) are inserted in the form of hinged arms for example to which the cameras are attached. To reduce the number of incisions, several cameras with different angles may be attached onto one same arm.

Provision may also be made for a frame that can be deployed, adapted so that it can be inserted via a trocar and then deployed inside the cavity 1, thereby forming a structure on which the cameras can then be attached. This latter solution has the advantage that there is no need to have one or more trocars dedicated to the structure.

The insertion and positioning of the cameras in the cavity may be carried out using a specific tool, consisting of a rigid tube optionally comprising several operator channels. The cameras are stored inside the distal part of the tube. In one possible configuration of the cameras, a stereoscopic head is used. A mechanism with semi-rigid cables can be provided to handle the camera support. This tool is compatible with most trocars used in conventional endoscopy. Sealing is ensured by a plug through which only the power and control cables for the stereoscopic head are able to pass. Deployment and removal are therefore ensured by a simple mechanism containing semi-rigid cables to allow pivoting of the stereoscopic head.

The cameras placed inside the cavity 1 allow 3D observation of a particular region of the operative site 2, at the chosen viewing angle, in relation to the chosen pair of cameras to form the stereoscopic sensor. The use of a plurality of cameras makes it possible to increase the virtual viewing angles offered to the practitioner without any need to modify the position of said cameras, which is particularly advantageous since this reduces the number of handling operations during surgery.

The image displayed by the display means 5, being constructed from data obtained from a multiple number of viewing angles, is of increased quality compared with existing systems which offer a single viewing angle (or at best under stereoscopic conditions) of the operative site.

Additionally, the image is perfectly stable since a 3D model is available which can be used to process the camera data to obtain 3D data, and by merging the data from all the cameras, a 2D or 3D image can be synthesized at the viewing angle desired by the practitioner.

It is noted that the quality of 3D reconstruction depends on the density of matched points, the quality of the reconstructed image being better the greater the number of points used. This density is dependent on the characteristics of the texture projected onto the operative site, and on available computing power. However, since the practitioner is essentially interested in one particular region of the operative site, it is sufficient to operate a 3D reconstruction on a relatively restricted number of points (e.g. a grid of 100 rows and 100 columns) and to carry out merging of camera data solely for the region of interest, using interpolation methods to synthesize an image of satisfactory resolution from the desired viewing angle or angles. This consequently brings a gain in data processing time without losing out on image quality since the region of interest is properly reconstructed.

Said imaging system has the further advantage of avoiding the practitioner's need to have recourse to mechanical control over the image capture means in order to observe a given region of the operative site. The practitioner effectively only needs to indicate the desired viewing angle (via any type of command whether vocal, touch or gyroscopic for example) without having to change the position of the cameras, and the corresponding image is immediately synthesized and displayed on the monitor. This also avoids having a surgical assistant specifically allocated to observation of the operative site since the practitioner has full, simple control over visualization of the operative site.

Finally, the proposed endoscopic imaging system allows major space savings in the operating room since it is no longer necessary to have a specific tool such as a robotic endoscope holder to control movement of the image capture means within the cavity 1 to capture the region of the operative site that it is desired to be viewed.

As indicated above, each pair of cameras may form a stereoscopic sensor allowing a certain quantity of 3D data to be obtained of a region of the operative site, so as to construct a 3D representation of this particular region.

The reconstruction of a 3D image of a particular region of the operative site is particularly advantageous since it does not require any contribution by the surgeon. The latter is directly provided with a virtual three-dimensional representation of the region under consideration. If the abdominal cavity is concerned for example, the 3D information obtained by the cameras can provide a 3D representation of the surface of the abdominal cavity. Visual re-transcription onto the monitoring screen is given by rendering of the 3D representation from a virtual viewing angle that can be directly controlled by the surgeon. To impart maximum realism to visualization, the 3D representation is textured with the original images given by the cameras.

To conduct 3D reconstruction, it is important to know the relative position of the two cameras forming the stereoscopic sensor so that it is possible to correlate more easily the data acquired by the two cameras.

There are several possibilities for determining this relative positioning of the cameras with respect to each other. The cameras may for example be carried by a mechanical device adapted so that it can be passed through the trocar and which after insertion in the abdominal cavity can be deployed in a predetermined relative position. Knowledge of the relative position of the cameras can also be acquired by particular image processing algorithms. Most often specially provided means are used to determine the relative position of the cameras.

It is possible for example to use a magnetic positioning device, placed inside or outside the cavity 1, permitting determination of the exact position of each camera. Said device may for example comprise a variable magnetic field source, located outside the human body, and two current loops attached to each camera. Field variations induce passing of a current in the current loops, this current being measured and allowing determination of the position and orientation of a camera.

Another solution consists of using an optic locating device. This device is formed so as to provide three reference points, fixed with respect to each other at least during the time of image acquisition. A non-deformable element may also be provided placed inside the cavity 1 so as that it lies in the field of vision of the at least two cameras forming the stereoscopic sensor under consideration, even by all the cameras placed inside the cavity 1, this non-deformable element being a reference point from which the relative positioning of the cameras can be determined. By non-deformable element is meant an element which, once in position inside the cavity does not undergo any deformations so that it can be used as reference. It is possible to provide an element which can be deformed as it is inserted in the cavity but whose shape remains fixed once it has been deployed inside the cavity.

Optic locating may also consist of a reference camera, arranged so that it is able to observe the cameras placed in the cavity. For this purpose, a camera may be used which is placed inside the cavity and has a widened field of vision so that it is able to observe all the cameras. This reference camera is fixed or at least in a position which can be determined with certainty with respect to a fixed reference point. Preferably two reference cameras are used to obtain more precise information. For example, two reference cameras can be provided preferably inside the cavity, each reference camera able to observe the other reference camera in addition to the cameras whose relative positioning is to be sought to ascertain. Another solution consists of connecting each of the cameras placed inside the cavity with a non-deformable reference member which extends outside the cavity so that it can be observed by the reference camera or cameras placed in this case outside the cavity.

It is also possible to determine the relative position of the cameras using projection means to project a texture onto a wall at the level of the operative site, this texture being adapted to form a basic reference system for the cameras. For example, a projector 9 may be used, inserted via a dedicated trocar 8 as shown in FIG. 1, which projects the pattern under consideration. This solution is also schematically illustrated in FIG. 4. As previously, the pattern projected by these projection means 9 must allow at least three points to be substantiated in the operative site.

FIG. 3 gives the diagram of one functioning mode of the endoscopic imaging system, or at least the diagram validating the endoscopy imaging system when it is set up for use during a surgical operation.

This diagram can be broken down into the following steps, whose order is of no importance:

Installing the cameras and textured light,
Collecting the video flow and recording the images,
Processing of the images,
Full calibration of the cameras,
Correction of distortions,
Epipolar geometry,
Optional correction of images,
Detection of points of interest (with and without textured light),
Search for matching points with epipolar constraint,
Elimination of poor matches,
3D reconstruction by triangulation,
Merging of data,
Surface extraction and texture mapping,
Image rendering of a virtual viewing angle,
Full validation.

Each of the different steps indicated above can be implemented using different methods available to the person skilled in the art. For this purpose, reference may be made to the following documents:

The publication by E. Prados and O. Faugeras titled "Handbook of Mathematical Models in Computer Vision" (Springer, 2006);

The publication by R. Horaud and F. Dornaika titled "Hand-Eye Calibration" (The International Journal of Robotics Research, Vol. 14, N° 3, pp. 195-210, June 1995);

The publication by R. I. Hartley and A. Zisserman titled "Multiple View Geometry in Computer Vision" (Cambridge University Press, 2000);

The publication by O. Faugeras titled "Three-Dimensional Computer Vision—A Geometric Viewpoint" (The MIT Press, Cambridge, Mass., USA, 1993);

The publication by R. Horaud and O. Monga titled "Vision par ordinateur: outils fondamentaux" (Second edition, revised and expanded, Editions Hermes, Paris, 1995);

The publication by Z. Zhang titled "A flexible new technique for camera calibration" (IEEE Transactions on Pattern Analysis and Machine Intelligence, 22(11):1330-1334, 2000);

The image processing library "OPEN CV" (see website http://www.intel.com/technology/computing/opencv/)

The image processing library "Camera Calibration Toolbox for Matlab" (see website http://www.vision.caltech.edu/bouguetj/calib_doc/)

The person skilled in the art will easily be able to adapt the methods described in these publications for the needs of the invention.

The reader will appreciate that numerous modifications can be made hereto without departing materially from the novel teachings and advantages described herein. Therefore, any modifications of this type are to be incorporated into the scope of the described endoscopic imaging system.

The invention claimed is:

1. An endoscopic imaging system for observation of an operative site within a volume located inside the body of an animal, comprising:

image capture means intended to provide information on the operative site;
processing means to process data provided by the image capture means,
display means to display data processed by the processing means, wherein:
the image capture means comprises at least three image capture devices positioned inside the volume, said image capture devices being cameras, with two of these three cameras being a pair and coupled to one another with a non-deformable member and being fixed to an instrument to be inserted inside the volume and the other one of the three cameras being independent and mobile relative to said two cameras, and wherein said pair of cameras forms a stereoscopic viewing system and:
the processing means comprises computing means to obtain three-dimensional data on the observed operative site based on data received from the image capture devices, and reconstruction means to reconstruct a three-dimensional image of a region of interest in the operative site based on the obtained three-dimensional data, further comprising means for determine the relative position of the cameras, wherein the means to determine the relative position comprises an optic locating device to locate the cameras, based on data derived from the cameras, wherein the optic locating device for the cameras comprises at least two reference cameras arranged within said volume so said reference cameras are able to observe the other cameras.

2. The system of claim 1, wherein the processing means further comprises synthesis means to synthesize an image of the region of interest, said synthesis means comprising means to merge the reconstructed three-dimensional image of the region of interest with data derived from the cameras on the region of interest, said data being interpolated to the desired resolution.

3. The system of claim 1, wherein the region of interest corresponds to an entire operative site.

4. The system of claim 1, wherein said system further comprises means to select a viewing angle, the display means comprising means to display the three-dimensional image corresponding to the selected viewing angle.

5. The system of claim 1, wherein the optic locating device for the cameras comprises a reference element arranged so that said optic locating device can be observed by at least two cameras.

6. The system of claim 1, wherein the means to determine the relative position comprises means to project a texture onto the operative site, so as to form a reference system for the cameras.

7. The system of claim 1, wherein the cameras are cameras having a volume of less than 5 mm$^3$.

8. The system of claim 1, wherein at least one of the cameras comprises an attachment device adapted to attach the at least one of the cameras to the body inside the volume.

9. The system of claim 6, wherein the means to project a texture onto the operative site is a light source.

10. The system of claim 8, wherein the attachment device comprises a first element fixed to the respective camera and a second separate element, the first and second elements able to be magnetically coupled, the second element being intended to remain outside the volume.

11. The system of claim 1, further comprising a mechanical structure intended to be placed inside the volume for attachment of at least one of the cameras.

12. The system of claim 11, wherein the mechanical structure is a frame adapted to be inserted via endoscopic route into the volume and able to be deployed inside the volume, said at least one of the cameras being configured to attach to said frame after the frame is deployed in said volume.

13. An endoscopic imaging system for observation of an operative site within a volume located inside the body of an animal, comprising:
   image capture means intended to provide information on the operative site; processing means to process data provided by the image capture means;
   display means to display data processed by the processing means, wherein:
   the image capture means comprising four cameras assembled as two pairs of cameras positioned inside the volume, each pair of cameras comprising two cameras securely fastened to one another, and each pair of cameras being independent and mobile relative to the other pairs of cameras, and wherein each pair of cameras forms a stereoscopic viewing system; and
   the processing means comprise computing means to obtain three-dimensional data on the observed operative site based on data received from the image capture devices, and reconstruction means to reconstruct a three-dimensional image of a region of interest in the operative site based on the obtained three-dimensional data, further comprising means for determine the relative position of the cameras, wherein the means to determine the relative position comprises an optic locating device to locate the cameras, based on data derived from the cameras, wherein the optic locating device for the cameras comprises at least two reference cameras arranged within said volume so said reference cameras are able to observe the other cameras.

14. The system of claim 11, wherein the mechanical structure intended to be placed inside the volume for attachment of the cameras is a hinged arm.

* * * * *

UNITED STATES PATENT AND TRADEMARK OFFICE
CERTIFICATE OF CORRECTION

PATENT NO. : 9,220,399 B2
APPLICATION NO. : 12/674594
DATED : December 29, 2015
INVENTOR(S) : Philippe Cinquin et al.

It is certified that error appears in the above-identified patent and that said Letters Patent is hereby corrected as shown below:

Title Page, Item (73) delete Assignee "CONSTELLIUM FRANCE" and replace with Assignee --UNIVERSITE JOSEPH FOURIER - GRENOBLE 1--

Signed and Sealed this
Seventeenth Day of May, 2016

Michelle K. Lee
*Director of the United States Patent and Trademark Office*